(12) United States Patent
Weizman

(10) Patent No.: US 8,050,742 B2
(45) Date of Patent: Nov. 1, 2011

(54) BIOPSY DEVICE

(75) Inventor: Patrick Weizman, Liberty Township, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 626 days.

(21) Appl. No.: 12/182,161

(22) Filed: Jul. 30, 2008

(65) Prior Publication Data

US 2010/0030106 A1    Feb. 4, 2010

(51) Int. Cl.
*A61B 6/00* (2006.01)
*A61B 5/05* (2006.01)
*A61B 10/00* (2006.01)

(52) U.S. Cl. .................. 600/431; 600/420; 600/562

(58) Field of Classification Search .................. 600/420, 600/431, 562, 567; 606/185; 604/59, 264
See application file for complete search history.

(56) References Cited

U.S. PATENT DOCUMENTS

| | | | |
|---|---|---|---|
| 421,072 A | 2/1890 | Harris | |
| 710,945 A | 10/1902 | Bunting | |
| 2,828,744 A | 4/1958 | Hirsch et al. | |
| 5,002,548 A | 3/1991 | Campbell et al. | |
| 5,024,727 A | 6/1991 | Campbell et al. | |
| 5,526,822 A | 6/1996 | Burbank et al. | |
| 6,228,055 B1 | 5/2001 | Foerster et al. | |
| 6,270,472 B1 | 8/2001 | Antaki et al. | |
| 6,347,241 B2 | 2/2002 | Burbank et al. | |
| 6,371,904 B1 | 4/2002 | Sirimanne et al. | |
| 6,450,938 B1 | 9/2002 | Miller | |
| 6,824,507 B2 | 11/2004 | Miller | |
| 6,889,833 B2 | 5/2005 | Seiler et al. | |
| 6,993,375 B2 | 1/2006 | Burbank et al. | |
| 6,996,433 B2 | 2/2006 | Burbank et al. | |
| 7,044,957 B2 | 5/2006 | Foerster et al. | |
| 7,047,063 B2 | 5/2006 | Burbank et al. | |
| 7,063,681 B1 | 6/2006 | Peery | |
| 7,229,417 B2 | 6/2007 | Foerster et al. | |
| 7,247,160 B2 | 7/2007 | Seiler et al. | |
| 7,322,360 B2 | 1/2008 | Fogarty et al. | |
| 7,329,414 B2 | 2/2008 | Fisher et al. | |
| 2003/0109803 A1 | 6/2003 | Huitema et al. | |
| 2005/0205445 A1 | 9/2005 | Seiler et al. | |
| 2005/0228311 A1 | 10/2005 | Beckman et al. | |
| 2006/0276680 A1 | 12/2006 | Seiler et al. | |
| 2007/0010738 A1 | 1/2007 | Mark et al. | |
| 2007/0016017 A1 | 1/2007 | Mark et al. | |
| 2007/0021714 A1 | 1/2007 | Miller | |
| 2007/0118048 A1 | 5/2007 | Stephens et al. | |
| 2008/0033280 A1 | 2/2008 | Lubock et al. | |
| 2008/0058637 A1 | 3/2008 | Fischell et al. | |
| 2008/0125766 A1 | 5/2008 | Lubock et al. | |

FOREIGN PATENT DOCUMENTS

EP    1545316 B1    1/2008

*Primary Examiner* — Michael Rozanski
(74) *Attorney, Agent, or Firm* — Frost Brown Todd LLC

(57) ABSTRACT

A biopsy device for marking a biopsy site is disclosed. The biopsy device can include a marker deployer and at least one marker disposed within an internal lumen of the deployer. The marker can include a non-metallic marker body sized and shaped to reduce variability in marker deployment force. In one embodiment, the marker body can be shaped to cooperate with a feature in the internal lumen of the deployer.

12 Claims, 5 Drawing Sheets

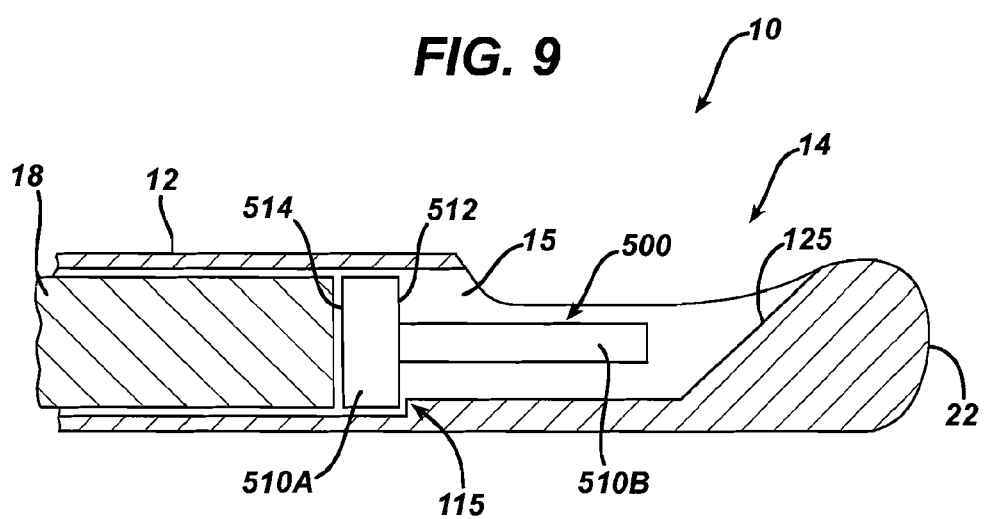
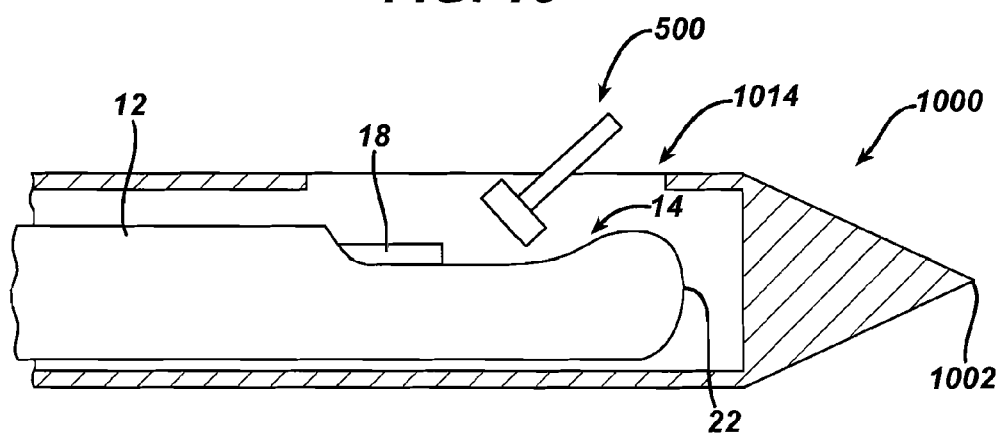

BIOPSY DEVICE

BACKGROUND

Biopsy samples have been obtained in a variety of ways in various medical procedures using a variety of devices. An exemplary biopsy device is the MAMMOTOME device from Ethicon Endo-Surgery, Inc. of Cincinnati, Ohio. Biopsy devices may be used under stereotactic guidance, ultrasound guidance, MRI guidance, or otherwise. Further exemplary biopsy devices are disclosed in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pub. No. 2003/0109803, entitled "MRI Compatible Surgical Biopsy Device," published Jun. 12, 2003; U.S. Pub. No. 2007/0118048, entitled "Remote Thumbwheel for a Surgical Biopsy Device," published May 24, 2007; U.S. Provisional Patent Application Ser. No. 60/869,736, entitled "Biopsy System," filed Dec. 13, 2006; U.S. Provisional Patent Application Ser. No. 60/874,792, entitled "Biopsy Sample Storage," filed Dec. 13, 2006; and U.S. Non-Provisional patent application Ser. No. 11/942,785, entitled "Revolving Tissue Sample Holder for Biopsy Device," filed Nov. 21, 2007. The disclosure of each of the above-cited U.S. patents, U.S. patent application Publications, U.S. Provisional Patent Applications, and U.S. Non-Provisional patent application is incorporated by reference herein.

In some settings, it may be desirable to mark the location of a biopsy site for future reference. For instance, one or more markers may be deposited at a biopsy site before, during, or after a tissue sample is taken from the biopsy site. Exemplary marker deployment tools include the MAMMOMARK, MICROMARK, and CORMARK devices from Ethicon Endo-Surgery, Inc. of Cincinnati, Ohio. Further exemplary devices and methods for marking a biopsy site are disclosed in U.S. Pub. No. 2005/0228311, entitled "Marker Device and Method of Deploying a Cavity Marker Using a Surgical Biopsy Device," published Oct. 13, 2005; U.S. Pat. No. 6,996,433, entitled "Imageable Biopsy Site Marker," issued Feb. 7, 2006; U.S. Pat. No. 6,993,375, entitled "Tissue Site Markers for In Vivo Imaging," issued Jan. 31, 2006; U.S. Pat. No. 7,047,063, entitled "Tissue Site Markers for In Vivo Imaging," issued May 16, 2006; U.S. Pat. No. 7,229,417, entitled "Methods for Marking a Biopsy Site," issued Jun. 12, 2007; U.S. Pat. No. 7,044,957, entitled "Devices for Defining and Marking Tissue," issued May 16, 2006; U.S. Pat. No. 6,228,055, entitled "Devices for Marking and Defining Particular Locations in Body Tissue," issued May 8, 2001; and U.S. Pat. No. 6,371,904, entitled "Subcutaneous Cavity Marking Device and Method," issued Apr. 16, 2002. The disclosure of each of the above-cited U.S. patents and U.S. patent application Publications is incorporated by reference herein.

U.S. Pat. No. 7,329,414 issued Feb. 12, 2008 to Fisher et al., incorporated by reference herein, discloses examples of polymers that swell in the presence of fluids, including polymers that are hydrogels.

It may be desirable to deploy markers from a cannula type deployer into the biopsy site. The force to deploy the marker should be predictable so that deployment of the marker is reliable. The marker should not unintentionally fall out of the deployer, and the force to deploy the marker should not be excessive. It is desirable to control the fit of the marker in the cannula to ensure the marker is deployed only when intended, and that the deployment force is not excessive. For instance, if the marker is too loose in the cannula, it may fall out before it is intended to be deployed. On the other hand, if the marker fits too tightly in the cannula, it may be difficult to deploy the marker from the exit of the cannula.

SUMMARY OF THE INVENTION

Applicant has recognized the need to accommodate certain variations in marker properties and/or marker dimensions while maintaining a predictable deployment force. For instance, certain marker materials, such as some non-metallic bioabsorble marker materials, may be formed from a material and/or be formed in such a way that the marker shape or size may change over time.

For example, some hydrogel markers can be formed in a mold, and then dehydrated. These dehydrated markers can become distorted upon dehydration. As a result, a marker molded or cast in a generally cylindrical shape can become deformed, such as into a curved or bowed shape. The curved or bowed shape of the marker may make it difficult to deploy the marker from the generally straight internal lumen of the deployer cannula. As a further complication, it can be desirable to expose the assembled marker deployer and marker to heat or radiation for sterilization purposes. Such sterilization procedures can result in further shape or dimension changes to the marker positioned within the cannula of the deployer.

One embodiment of the present invention provides a biopsy marker having a marker body with first and second portions. The first and second portions of the marker body may be sized and shaped relative to one another and the internal lumen of the marker deployer to reduce the effect of dimensional stability as a factor in deployment of the marker.

The marker body can have a total axial length LT, the first marker portion can have a length L1 and width D1, and the second marker portion can have a length L2 and width D2, where L1 is greater than L2, D2 is greater than D1, and LT/L2 is greater than about 1.5.

In another embodiment, the invention provides a marker deployer having an internal lumen comprising a retaining feature, and a marker disposed in the lumen. The retaining feature engages the marker to restrict distal motion of the marker in the lumen, and the marker extends both proximally and distally of the retaining feature.

BRIEF DESCRIPTION OF THE DRAWINGS

It is believed the present invention will be better understood from the following description of certain examples taken in conjunction with the accompanying drawings, in which like reference numerals identify the same elements and in which:

FIG. 9 depicts a marker according to the present invention disposed within the internal lumen of a marker deployer FIG. 10 depicts a marker according to the present invention being deployed from a deployer and through a lateral tissue receiving port in a biopsy needle to mark a biopsy site.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Figure 1:
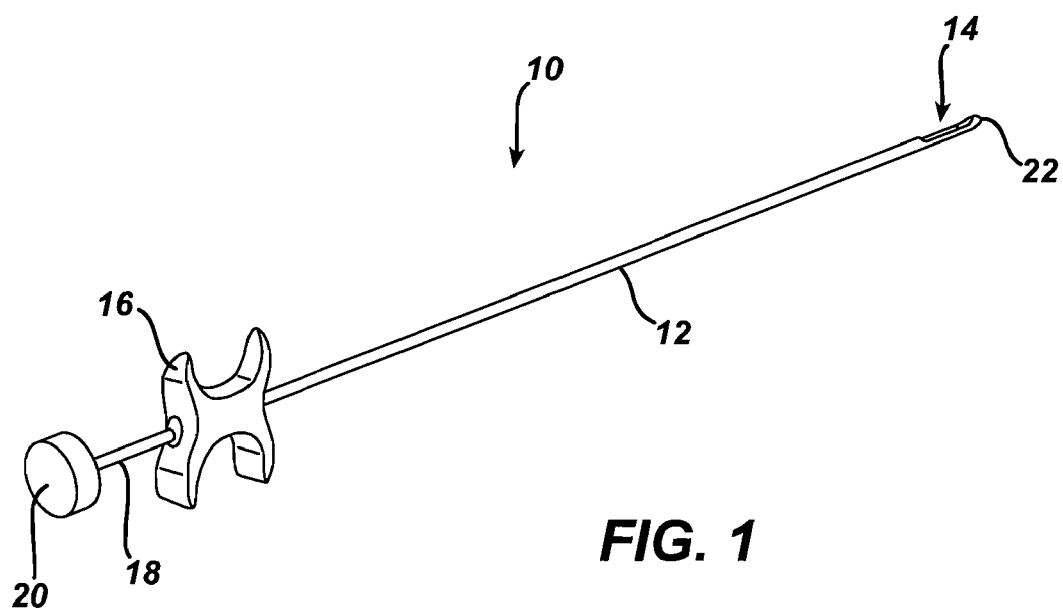
FIG. 1 depicts a perspective view of a marker deployer.

FIG. 1 illustrates a marker deployer 10 which includes an elongate outer cannula 12 having a marker exit, such as side opening 14 formed near to, but spaced proximally from, the distal end of the cannula 12. The distal end of cannula 12 can include a closed tip 22, though in other embodiments, the cannula 12 can have an open distal end, and the open distal end can serve as the marker exit. The cannula 12 includes an internal lumen extending axially through at least a portion of the length of the cannula 12 and communicating with the marker exit.

A grip 16 can be provided at the proximal end of cannula 12. Cannula 12 and tip 22 may be formed of any suitable material, including polymeric materials, metals, and the like. A push rod 18 can be provided, with push rod 18 extending coaxially in cannula 12 such that the push rod 18 is configured to translate within cannula 12. Rod 18 can have sufficient rigidity in compression to push a marker from the internal lumen of cannula 12 out through opening 14, yet be relatively flexible in bending. A plunger 20 can be provided at the proximal end of rod 18 for forcing rod 18 distally in cannula 12.

A user may grasp grip 16 with two fingers, and may push on plunger 20 using the thumb on the same hand, so that the deployer 10 can be operated by a user's single hand. A spring (not shown) or other feature may be provided about rod 18 to bias rod 18 proximally relative to grip 16 and cannula 12.

Figure 2:
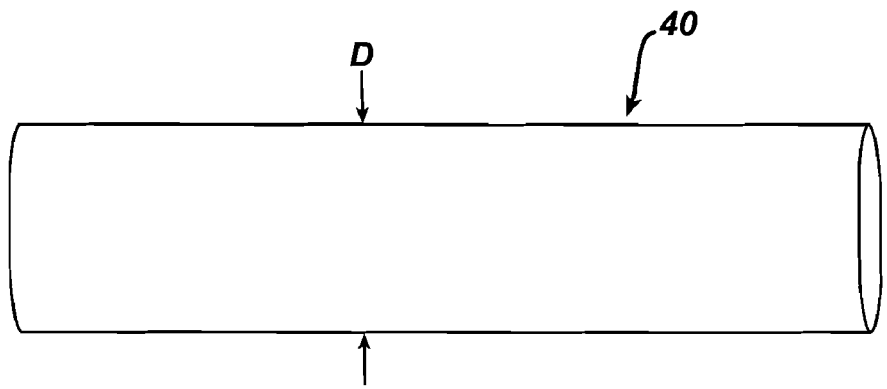
FIG. 2 depicts a marker having a generally uniform cylindrical cross section.
Figure 3:
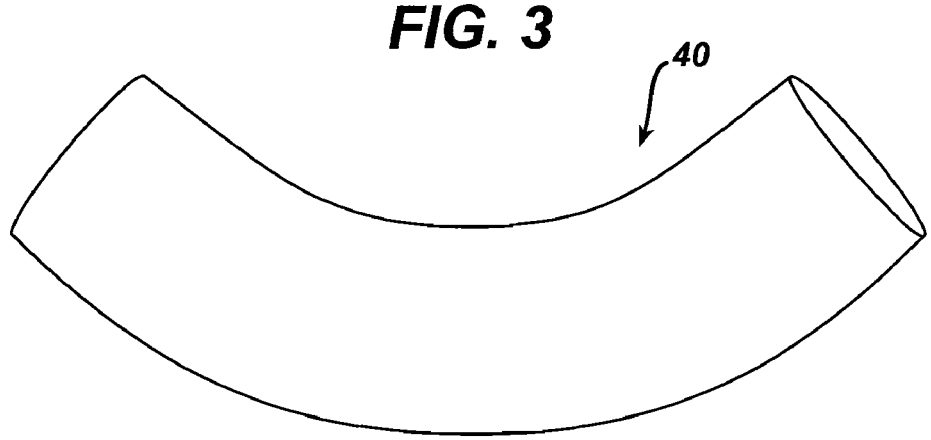
FIG. 3 depicts distortion that may occur in a marker such as the marker of FIG. 2.

FIG. 2 illustrates a marker 40 having a marker body having a generally uniform diameter cylindrical cross-section. The diameter D of the marker 40 can be sized to provide a slight compression fit within the internal lumen, or the diameter D can be sized to be slightly smaller than the internal diameter. When the marker body of such a marker 40 is formed of certain materials, the shape and/or dimensions of the marker may change or otherwise become unstable depending temperature, humidity, or other environmental or time dependent conditions. For instance, FIG. 3 illustrates how the marker 40 may become distorted to take on a bowed shape, such as may occur when a molded marker is removed from the mold, during the dehydration process, or when the marker is sterilized after being loaded into the deployer 10 and packaged. Such changes in dimension and/or shape can negatively impact the force to deploy the marker from the cannula 12, such as by increasing the force required to deploy the marker, or by making the force to deploy the marker vary in an unacceptable manner.

FIGS. 4-8 illustrate various marker embodiments of the present invention. The markers illustrated in FIGS. 4-8 have a marker body comprising at least two marker body portions, with one marker body portion having a relatively short axial length, and having a relatively wider cross-sectional dimension (for example a larger diameter) than at least one other marker body portion. The width (or diameter) of the marker body portion having the relatively larger width and relatively short length can be sized to provide the desired fit in the internal diameter of the internal lumen of the cannula. Because this marker body portion has a relatively short axial length, bowing or distortion of the body portion will have less impact on the force to deploy the marker. Distortion of the marker body portion having the relatively smaller width (e.g. smaller diameter) and relatively longer axial length may occur, but because of the relatively smaller width of this portion, distortion of this marker body portion will tend to have little or no impact on the force to deploy the marker.

Figure 4:
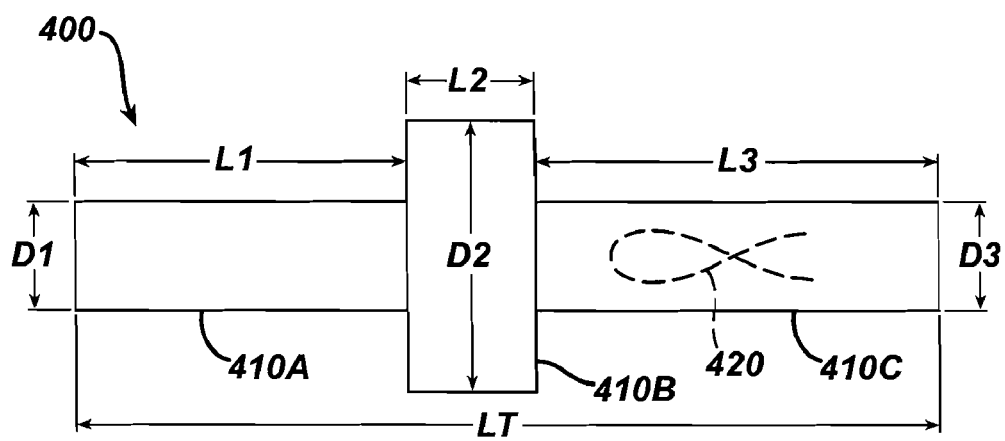
FIG. 4 depicts a marker having a marker body according to one embodiment of the present invention, including three marker body portions.

Referring to FIG. 4, a marker 400 according to one embodiment of the present invention can have a marker body formed of a non-metallic material, such as a molded, dehydrated hydrogel material which is swellable upon contact with body fluids. For example, the marker body can be a biodegradable natural or synthetic hydrogel, such as disclosed in U.S. Pat. No. 7,329,414 issued Feb. 12, 2008 to Fisher et al., which patent is incorporated herein by reference. The marker body can include a contrasting agent for imaging, or alternatively, the marker body can carry a metallic marker element as described in more detail below.

The marker body can have a total axial length LT. It is desirable that the total length LT of the marker body be at least about 1 centimeter (as measured prior deployment of the marker and prior to any swelling or rehydration of the marker) to aid in visualizing the marker in the body using one or more imaging methods, such as X-ray, ultrasound, or Magnetic Resonance Imaging (MRI).

The marker body can include a first marker body portion 410A, a second marker body portion 410B, and a third marker body portion 410C. The body portions 410A-410C can be molded or cast together to form an integral, unitary marker body. Alternatively, the body portions could be formed separately and joined together during a subsequent manufacturing operation.

Marker body portion 410A can have a generally cylindrical shape with a generally uniform diameter D1 and an axial length L1. Marker body portion 410B can have a generally cylindrical shape with a generally uniform diameter D2 and an axial length L2. Marker body portion 410C can have a generally cylindrical shape with a generally uniform diameter D3 and an axial length L3. The ratio of LT/L2 is at least about 1.5, and can be at least about 4 in one embodiment. D2 is greater than D1, and D2 is greater than D3. The ratio D2/D1 can be at least about 1.5, and similarly, the ratio D2/D3 can be at least about 1.5. D1 and D3 may be, but are not necessarily, substantially equal, and L1 and L3 may be, but are not necessarily, substantially equal. The ratio of L1/D1 and L3/D3 can each be at least about 2.5. A relatively large ratio of L1/D1 and L3/D3 can assist in providing a relatively low bending stiffness of the respective body portions 410A and 410C. Without being limited by theory, a relatively low bending stiffness of body portions 410A and 410C can be desirable so that the contribution of these body portions to the deployment force will be minimized. The ratio of L2/D2 can be less than both L1/D1 and L3/D3, and can be less than about 1. In particular, in one or more embodiments the ratio L2/D2 can be less than about 0.5.

In one particular non-limiting example, LT can be about 1.25 centimeters, L1 can be about 0.55 centimeters, L2 can be about 0.15 centimeters, L3 can be about 0.55 centimeters, D1 can be about 0.15 centimeters, D2 can be about 0.3175 centimeters, and D3 can be about 0.15 centimeters.

Without being limited by theory, it is believed the marker 400 shown in FIG. 4 has the advantage that the central marker body portion 410B having the relatively larger diameter D2 provides fit of the marker within the internal lumen of the cannula 12. The marker body portions extending proximally and distally from central body portion 410B (portions 410A and 410C) may become distorted or bowed with little or no impact on marker fit and deployment force, due at least in part because of the relatively smaller diameters D1 and D3 and the relatively low bending stiffness of body portion 410A and 410C.

While the marker body portions in FIG. 4 are shown as being generally cylindrical portions having generally circular cross-sections, other geometries and cross-sections can be employed. For instance, the marker body could have oval, rectangular, triangular, or other suitable cross-sectional provided such shapes are generally compatible with the internal lumen of the cannula 12.

Marker 400 may also carry one or more radiopaque marker elements, such as on the surface of the marker body (for example as a ring encircling one of the marker body portions), or inside the marker body. In FIG. 4, a marker element 420 in the form of a twisted metallic wire is shown in phantom, as being embedded inside marker body portion 410C, though the marker could be located in the central marker body portion 410B, or in body portion 410A. Radiopaque marker materials, such as titanium, stainless steel, gold, silver, and any other suitable radiopaque material may be employed.

Figure 5:
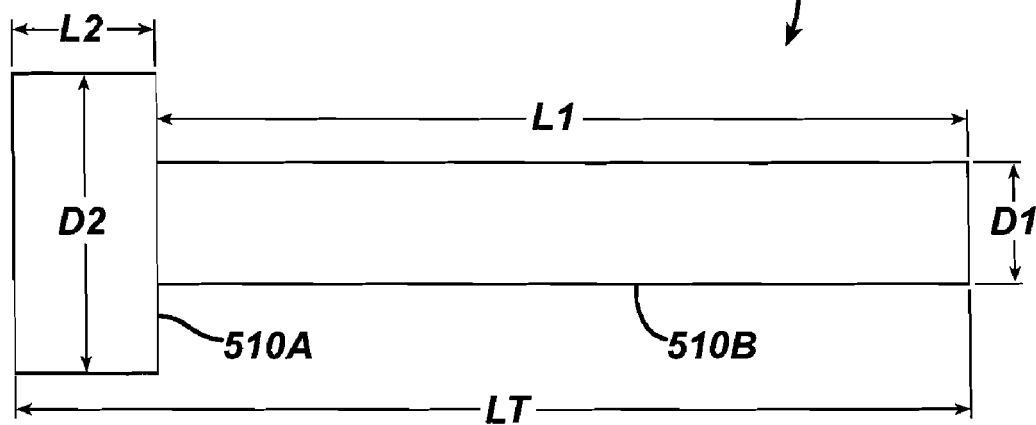
FIG. 5 depicts a marker according to another embodiment of the present invention and having two marker body portions.

FIG. 5 illustrates a marker 500 according to another embodiment of the present invention. Marker 500 has a marker body with axial length LT and comprising two marker body portions 510A and 510B. Body portion 510A has a length L2 and a diameter D2, and body portion 510B has length L1 and diameter D1. The ratio of LT/L2 is at least about 1.5, and can be at least about 8 in one embodiment. D2 is greater than D1, the ratio D2/D1 can be at least about 1.5, and in one embodiment D2/D1 is at least about 2. In one particular non-limiting example, LT can be about 1.25 centimeters, L1 can be about 1.1 centimeters, L2 can be about 0.15 centimeters, D1 can be about 0.15 centimeters, and D2 can be about 0.3175 centimeters.

Without being limited by theory, it is believed the marker 500 shown in FIG. 5 has the advantage that a relatively larger diameter body portion is positioned at the proximal end of the marker, so that there is a relatively larger surface area for contact with the push rod 18. Additionally, the relatively larger diameter body portion can have a surface to engage a feature associated with the internal surface of the lumen 15, as described in more detail below.

Figure 6:
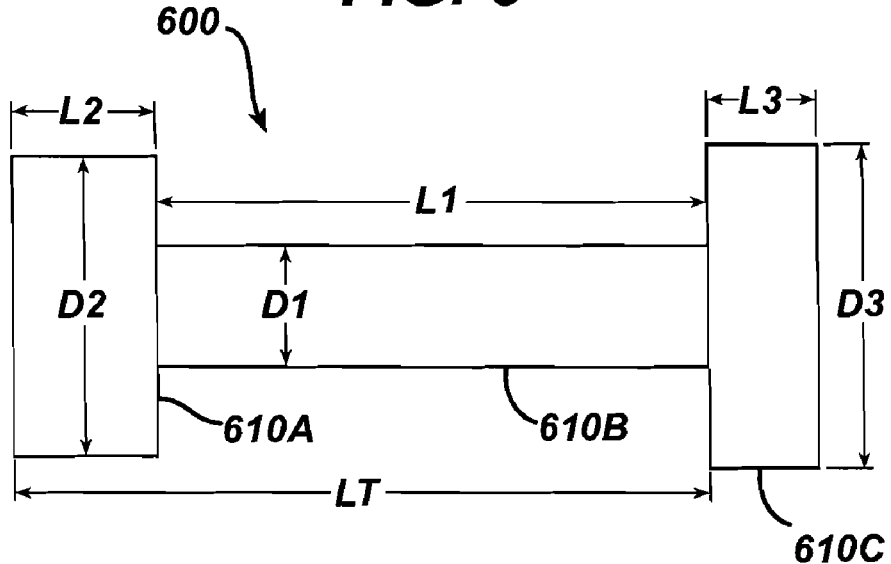
FIG. 6 depicts a marker according to another embodiment of the present invention, and having three marker body portions.

FIG. 6 illustrates an embodiment of a marker 600 according to the present invention having a marker body with an axial length LT and comprising three body portions 610A, 610B, and 610C. The ratio of LT/L2 and the ratio of LT/L3 can each be at least about 1.5, and in one embodiment, L2 and L3 are substantially equal and the ratio LT/(L2+L3) is at least about 1.5. D2 and D3 are each greater than D1, and in one embodiment D2 and D3 are substantially equal and the ratios D2/D1 and D3/D1 are both at least about 1.5. In one particular non-limiting example, LT can be about 1.25 centimeters, L1 can be about 0.95 centimeters, L2 can be about 0.15 centimeters, L3 can be about 0.15 centimeters, D1 can be about 0.15 centimeters, D2 can be about 0.3175 centimeters, and D3 can be about 0.3175.

Without being limited by theory, it is believed the marker 600 shown in FIG. 6 has the advantage that relatively larger diameter body portions disposed at both the proximal and distal ends of the marker body may be helpful in centering the marker within the internal lumen and stabilizing the marker during deployment.

Figure 7:
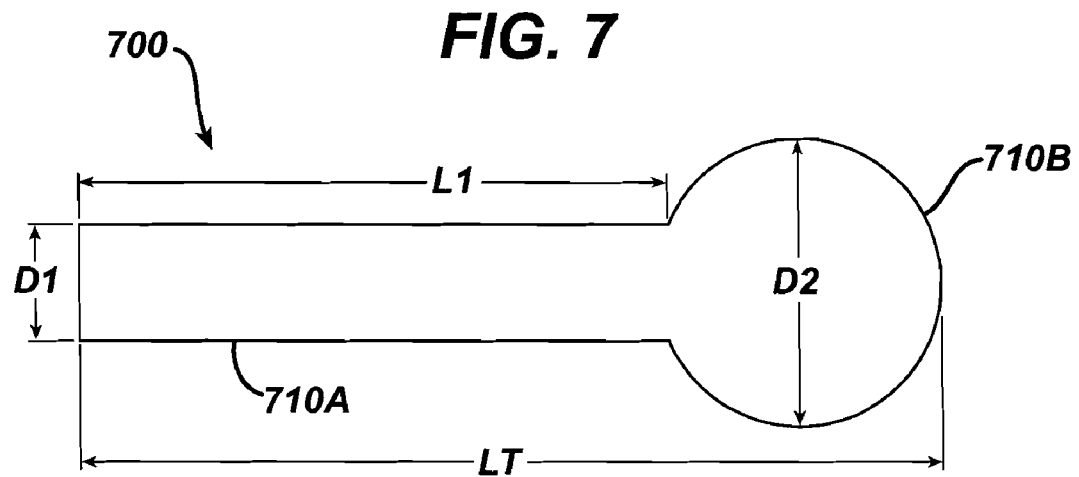
FIG. 7 depicts a marker according to another embodiment of the present invention, and having a generally cylindrical marker body portion and a generally spherical marker body portion, with the cylindrical body portion having a length greater than the diameter of the spherical portion, and a diameter less than that of the spherical body portion.

FIG. 7 illustrates an embodiment of a marker 700 according to the present invention having a marker body with axial length LT and comprising two marker body portions 710A and 710B. Marker body portion 710 is generally cylindrical, and has a diameter D1 and a length L1. Marker body portion 710 can be generally spherical, and can have a diameter D2 which is greater than D1. LT/D2 is at least about 1.5, and in one embodiment is at least about 4.0. The ratio of D2/D1 can be at least about 1.5, and in one embodiment is at least about 2. In an alternative embodiment, generally spherical body portions can be disposed at both the proximal and distal ends of a generally cylindrical body portion.

Figure 8:
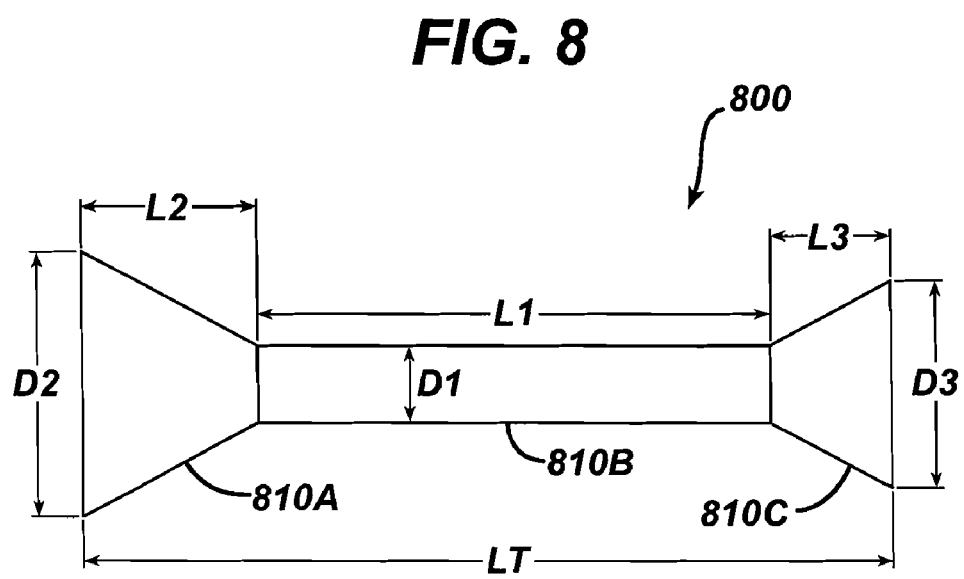
FIG. 8 depicts a marker according to another embodiment of the present invention, and having a generally cylindrical body portion extending between two generally conically shaped body portions.

FIG. 8 illustrates an embodiment of a marker 800 according to the present invention having a marker body with an axial length LT and comprising three body portions 810A-810C. Marker body portions 810A and 810C have the shape of truncated cones, and marker body portion 810B has a generally cylindrical shape. The ratio LT/L1 is at least about 1.5, and in one embodiment is at least about 4. The maximum diameters D2 and D3 of the truncated cone portions can be generally equal, and the ratios D2/D1 and D3/D1 can be at least about 1.5. In an alternative embodiment, the truncated cone portions 810A and 810C can be oriented (e.g. reversed) such that the maximum diameter base of each cone is adjacent the body portion 810B.

FIG. 9 illustrates a marker 500 of the type shown in FIG. 5 disposed within an internal lumen 15 of outer cannula 12. The internal surface of the lumen 15 is shaped or otherwise formed to include a retaining feature to restrict the marker 500 from inadvertently falling out of the deployer, or otherwise being inadvertently deployed without actuation of the push rod 18. In FIG. 9, the retaining feature shown is provided by a step, or ledge 115, formed in the internal surface of the lumen 15. The ledge 115 can be positioned in a bottom portion of the lumen 15, and can be disposed proximally of a ramp 125. The ramp 125 aids in directing a marker out of side opening 14 when push rod 18 is advanced distally by a user. Alternatively, the ledge 115 can be positioned on a top or side portion of the inside surface of the lumen.

Still referring to FIG. 9, the marker body portion 510A has an annular surface 512 that faces generally distally, and a generally circular surface 514 facing proximally. The Marker 500 can be held in place in the internal lumen 15, with push rod 18 abutting, or adjacent to surface 514, and ledge 115 abutting, or adjacent to surface 512.

The ledge 115 is dimensioned relative to the diameter of the marker and the nominal internal diameter of lumen 15 such that, when push rod 18 is advanced distally by the user, the marker body portion 510A can be slightly compressed or otherwise deform such that the marker 500 is pushed over the ledge 115. Continued force on the push rod causes the marker to be advanced distally to contact ramp 125 and then to be laterally displaced out of the side opening 14.

Generally, the radial height of ledge 115 can be less than the difference D2−D1, and in one embodiment the radial height of ledge 115 is less than about (D2−D1)/2. If desired, the distal end of marker body portion 510B can be rounded or beveled to aid in moving the marker upward along ramp 125. Additionally, the circular edge of marker body portion 510A adjacent surface 512 can be chamfered slightly to aid in pushing the marker over ledge 115.

If desired, the retaining feature can be provided by other structures, such as by one or more projections extending from the interior surface of the lumen 15, or by a distal section of the lumen having an internal diameter slightly smaller than an internal diameter of a proximal portion of the lumen 15. Also, the marker can be configured such that one marker body portion separates from the marker when the push rod 18 is advanced to push the marker distally beyond the retaining feature. For instance, in FIG. 9, the marker body portion 510A could be joined to the body portion 510B such that when the push rod is advanced, the portion 510A engages the ledge 115 and is torn, sheared, or otherwise separated from body portion 510B.

In FIG. 9, only one marker is shown disposed in deployer 10. However, it will be understood that multiple markers can be disposed in deployer 10, such as in an end to end configuration. The markers can have the same size and shape, or alternatively have different sizes and/or shapes.

The marker deployer 10 may be used to deploy a marker to mark a particular location within a patient. Referring to FIG. 10, a cannular biopsy needle 1000 is shown. The needle 1000 is shown having a closed distal end with piercing tip 1002, and a lateral tissue receiving aperture 1014. Marker deployer 10 may be introduced to a biopsy site through biopsy needle 1000, which can be the same needle used to collect a tissue sample from the biopsy site. The biopsy needle 1000 can be of the type used with single insertion, multiple sample vacuum assisted biopsy devices. Several such biopsy devices are disclosed in the various patents and patent applications that have been referred to and incorporated by reference herein, though any other biopsy devices may be used.

FIG. 10 shows the distal end of a marker deployer 10 disposed within the needle 1000. The needle 1000 can be positioned in tissue, and a biopsy sample can be obtained through opening 1014, thereby providing a biopsy cavity adjacent opening 1014. Then, without removing the needle 1000, the deployer 10 can be inserted into a proximal end of the needle 1000. In FIG. 10, the needle 1000 and deployer 10 are positioned such that opening 14 of cannula 12 and opening 1014 of needle 1000 are substantially aligned axially and circumferentially. Then, with the deployer and needle so positioned at the biopsy site, the push rod 18 can be advanced to deploy the marker up the ramp 125, through the opening 14, and then through 1014, into the biopsy cavity.

Embodiments of the devices disclosed herein are generally designed to be disposed of after a single use, but could be designed to be used multiple times. After forming the marker, and inserting the marker into the deployer, the biopsy device can be sterilized. The device can be placed in a package, such as plastic or TYVEK bag.

The packaged biopsy device may then be placed in a field of radiation such as gamma radiation, x-rays, or high-energy electrons to sterilize the device and packaging. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed:

1. A biopsy device comprising:
   a marker deployer having an axially extending internal lumen; and
   at least one marker disposed within the internal lumen of the deployer, wherein the marker comprises:
      a marker body having an axial length LT, and wherein the marker body comprises:
         a first marker portion having a length L1 and a width D1,
         a second marker portion having a length L2 and width D2, and
         a third marker portion,
         wherein D2 is greater than D1, and
         wherein LT/L2 is at least about 1.5,
      wherein the first marker portion and the second marker portion together define a T shape,
      wherein the second marker portion is disposed between the first and third marker portions,
      wherein the first and third marker portions are configured to be substantially free of engagement with the internal lumen of the deployer while the marker is within the internal lumen.

2. The biopsy device of claim 1 wherein the ratio of LT/L2 is at least about 2.

3. The biopsy device of claim 2 wherein the ratio of LT/L2 is at least about 4.

4. The biopsy device of claim 1 wherein the ratio of D2/D1 is at least about 1.5.

5. The biopsy device of claim 1 wherein the first and second marker portions comprise an integral, unitary marker body.

6. The biopsy device of claim 1 wherein the first and second marker portions comprise a hydrogel.

7. The biopsy device of claim 1 wherein the first and second marker portions comprise a dehydrated material configured to swell upon contact with body fluids.

8. The biopsy device of claim 1 wherein the first and second marker portions have generally circular cross-sections.

9. The biopsy device of claim 1 wherein the internal lumen of the deployer has a retaining feature for engaging a distally facing surface of one of the marker portions.

10. The biopsy device of claim 1 further comprising a radiopaque element carried by at least one of the first and second marker portions.

11. A biopsy device comprising:
    a marker deployer having an axially extending internal lumen; and
    at least one marker disposed within the internal lumen of the deployer, wherein the marker comprises:
       a marker body having an axial length LT, and wherein the marker body comprises:
          a first marker portion having a length L1 and a width D1,
          a second marker portion having a length L2 and width D2, and
          a third marker portion,
          wherein L1 is greater than L2, D2 is greater than D1, and
          LT/L2 is at least about 1.5, wherein the first marker portion comprises a first discrete exterior surface area, wherein the second marker portion comprises a second discrete exterior surface area, and wherein the first discrete exterior surface area and the second discrete exterior surface area are adjacent to each other, wherein the second marker portion is disposed between the first and third marker portions, wherein the first and third marker portions are configured to be substantially free of engagement with the internal lumen of the deployer while the marker is within the internal lumen.

12. A biopsy device comprising:

a marker deployer having an axially extending internal lumen; and at least one marker comprising hydrogel and disposed within the internal lumen of the deployer;

wherein the marker comprises a first marker body portion, a second marker body portion, and a third marker body portion;

wherein the second marker body portion is disposed between the first and third marker body portions;

wherein the diameter of the second marker body portion is greater than the diameter of the first marker body portion and the diameter of the second marker body portion is greater than the diameter of the third marker body portion; and wherein the axial length of the second marker body portion is less than the axial length of the first and third marker body portions, wherein the first and third marker body portions are configured to be substantially free of engagement with the internal lumen of the deployer while the marker is within the internal lumen.

* * * * *